US007867976B2

(12) United States Patent
Steinman et al.

(10) Patent No.: US 7,867,976 B2
(45) Date of Patent: Jan. 11, 2011

(54) NOGO EPITOPIC FRAGMENTS FOR MODULATING IMMUNE RESPONSE

(75) Inventors: Lawrence Steinman, Stanford, CA (US); Hideki Garren, Palo Alto, CA (US); Paulo Fontoura, Lisbon (PT)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 833 days.

(21) Appl. No.: 10/556,756

(22) PCT Filed: May 14, 2004

(86) PCT No.: PCT/US2004/015387

§ 371 (c)(1),
(2), (4) Date: Jun. 1, 2007

(87) PCT Pub. No.: WO2004/110353

PCT Pub. Date: Dec. 23, 2004

(65) Prior Publication Data

US 2007/0280954 A1 Dec. 6, 2007

Related U.S. Application Data

(60) Provisional application No. 60/470,593, filed on May 15, 2003.

(51) Int. Cl.
*A61K 38/16* (2006.01)
*A61K 38/00* (2006.01)
*C07K 14/00* (2006.01)
*C07K 14/435* (2006.01)

(52) U.S. Cl. .............................. 514/13; 514/2; 530/300; 530/326

(58) Field of Classification Search .................. None
See application file for complete search history.

(56) References Cited

U.S. PATENT DOCUMENTS 7,119,165 B2 * 10/2006 Strittmatter ................. 530/350
7,560,102 B2 * 7/2009 Eisenbach-Schwartz et al. . 424/93.1

OTHER PUBLICATIONS

Fontoura, Paulo, et al., "Immunity to the Extracellular Domain of Nogo-A Modulates Experimental Autoimmune Encephalomyelitis", *The Journal of Immunology*, Dec. 2004, vol. 173, No. 11, pp. 6981-6992.
Hauben, Ehud, et al., "Vaccination with a Nogo-A-derived peptide after incomplete spinal-cord injury promotes recovery via a T-cell-mediated neuroprotective response: Comparison with other myelin antigens", Proc. Natl. Acad. Sci. USA. vol. 98, No. 26, pp. 15173-15178, Dec. 2001.

* cited by examiner

*Primary Examiner*—Christine J Saoud
*Assistant Examiner*—Jon M Lockard
(74) *Attorney, Agent, or Firm*—Bozicevic, Field & Francis LLP; Pamela J. Sherwood (57) ABSTRACT

Epitopic fragments of Nogo, including Nogo 45-66, elicit a specific and strong T cell response, and a B cell response. T cells reactive to Nogo antigens are capable of ameliorating ongoing disease, which may be induced with other antigens. The present invention provides compositions and methods for the identification and use of Nogo epitopic fragments in the treatment of immune related disease.

1 Claim, 6 Drawing Sheets

Figure1. Experimental Autoimmune Encephalomyelitis in Nogo-/- mice.

Figure 2. Experimental Autoimmune Encephalomyelitis induced with Nogo66 peptides.

T cell Proliferative response.

Figure 3. Antibody response against myelin antigens after EAE induction with Nogo peptides

A. Myelin microarray of serum antibodies a Normal Mouse Serum b Ng 45-66 Induced c Ng 1-22 Induced

B. Cluster analysis.

C. Epitope spreading from Nogo

| | a. Normal | b. Nogo 45-66 | c. Nogo 1-22 |
|---|---|---|---|
| Anti-mouse IgG/M | 50000 | 50000 | 50000 |
| CCP cyc 0112-15 | 161 | 16261 | 41 |
| CCP lin 0116-35 | 69 | 8066 | 43 |
| mMAG 193-208 | 99 | 2978 | 57 |
| mMAG 313-328 | 33 | 9874 | 49 |
| MBP 87-99 | 37 | 19 | 4018 |
| MBP89-101 91Ala | 180 | 133 | 4990 |
| hMBP 121-139 | 26 | 3937 | -26 |
| HS VP16-MBP | 44 | 2591 | 150 |
| MOG 35-55 | 179 | | 367 |
| BI MOG35-55 BIOTIN | 5 | | -21 |
| MOG 35-55 F | 105 | | 33 |
| Nogo 1-22 | -14 | 44 | 5401 |
| Nogo 11-30 | 8 | 61 | 3379 |
| Nogo 45-66 | -10 | 25658 | -22 |
| Ng 53-66 +10 | 30 | 211 | 537 |
| mOSP 32-51 | -95 | 825 | -92 |
| Mouse P2 79-98 | 42 | 851 | 253 |
| P2 99-120 | 127 | 563 | 9315 |
| HS VP16-PAP7 | 147 | 2070 | 391 |

Figure 4. Anti-Nogo reactive T cell lines exhibit normal activation markers.

Figure 5. Nogo peptides do not cross react with other myelin antigens.

A. PLP139-151 T cell lines and Nogo specific T cell lines do not cross-react.

B. Primary structure comparison between PLP139-151, MOG35-55 and Nogo66 peptides Figure 6. Adoptive transfer of anti-Nogo reactive T cell lines ameliorates EAE in SJL/J mice.

A. Adoptive transfer of anti-Nogo reactive T cell lines does not induce EAE.

B. Adoptive transfer of anti-Nogo reactive T cell lines ameliorates EAE.

C. Anti-Nogo reactive T cell can exhibit protective T helper phenotypes.

SEQUENCE LISTING

```
<160> NUMBER OF SEQ ID NOS: 5

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence:
      demyelinating autoimmune disease ordered am

```
<223> OTHER INFORMATION: Xaa = Lys or absent
<220> FEATURE:
<221> NAME/KEY: MOD_RES
<222> LOCATION: (21)
<223> OTHER INFORMATION: Xaa = Glu or absent
<220> FEATURE:
<221> NAME/KEY: MOD_RES
<222> LOCATION: (22..23)
<223> OTHER INFORMATION: Xaa = Tyr or absent
<220> FEATURE:
<221> NAME/KEY: MOD_RES
<222> LOCATION: (24)
<223> OTHER INFORMATION: Xaa = Lys or absent

<400> SEQUENCE: 1

Glu Tyr Tyr Lys Xaa Xaa Xaa Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence:Nogo-A
      (reticulon 4a, RTN4a) synthetic epitopic peptide
      Nogo45-66

<400> SEQUENCE: 2

Val Asn Ser Thr Ile Lys Glu Leu Arg Arg Leu Phe Leu Val Asp Asp
 1               5                  10                  15

Leu Val Asp Ser Leu Lys
            20

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence:Nogo-A
      (reticulon 4a, RTN4a) synthetic epitopic peptide
      Nogo45-66

<400> SEQUENCE: 3

Val Asn Cys Thr Ile Lys Glu Leu Arg Arg Leu Phe Leu Val Asp Asp
 1               5                  10                  15

Leu Val Asp Ser Leu Lys
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence:Nogo-A
      (reticulon 4a, RTN4a) synthetic epitopic peptide
      Nogo1-22

<400> SEQUENCE: 4

Arg Ile Tyr Lys Gly Val Ile Gln Ala Ile Gln Lys Ser Asp Glu Gly
 1               5                  10                  15

His Pro Phe Arg Ala Tyr
            20

<210> SEQ ID NO 5
<211> LENGTH: 22
```

```
<212> TYPE: PRT
<213> ORGANISM: Artificial Sequence
<220> FEATURE:
<223> OTHER INFORMATION: Description of Artificial Sequence:Nogo-A
      (reticulon 4a, RTN4a) synthetic epitopic peptide
      Nogo23-44

<400> SEQUENCE: 5

Leu Glu Ser Glu Val Ala Ile Ser Glu Leu Val Gln Lys Tyr Ser
 1               5                  10                  15

Asn Ser Ala Leu Gly His
            20
```

NOGO EPITOPIC FRAGMENTS FOR MODULATING IMMUNE RESPONSE

CROSS-REFERENCES TO RELATED APPLICATIONS

This is a U.S. National Phase Application under 35 U.S.C. §371 of International Application No. PCT/US2004/015387, filed May 14, 2004, which claims benefit of U.S. Provisional Application No. 60/470,593, filed May 15, 2003, which is incorporated by reference herein in its entirety.

Autoimmune disease results from the misdirection of an immune response to target healthy cells and/or tissues of the body. Autoimmune diseases are characterized by T and B lymphocytes that react with self-molecules, including polypeptides, nucleic acids, small nuclear particles, and the like. Autoimmune diseases include diseases that affect specific tissues, as well as diseases that can affect multiple tissues, depending in part on the distribution of the autoantigen(s).

The Nogo protein is a member of the Reticulon (RTN) family that has been recently identified as a major myelin-associated neurite regrowth inhibitor specific to central nervous system (CNS) myelin (Chen 2000, GrandPré 2000). Nogo-A is the longest of three alternatively produced transcripts of the nogo gene, with 1,163 amino-acid residues, and is specific to the CNS. All three isoforms contain a predicted extracellular 66-amino acid loop in their C-terminus end, to which most of the inhibitory capacity has been attributed. This extracellular loop called Nogo-66 acts through interaction with the Nogo receptor and a p75 co-receptor and mediates neurite growth inhibition by antagonistic regulation of intracellular signaling through RhoA and Rac1(Fournier 2001, Brittis 2001, Wang 2002a, Niederost 2002).

Other myelin proteins that have also been implicated in regrowth inhibition, such as myelin-associated glycoprotein (MAG) and oligodendrocyte-myelin glycoprotein (OMgp) also act by signaling through the Nogo receptor system (Liu 2002, Wang 2002b).

Several therapeutic strategies aimed at improving axonal regeneration have attempted to block interaction in the Nogo-Nogo receptor system (Karim 2001). These have included using the recombinant monoclonal antibody IN-1 which recognizes Nogo-A (Merkler 2000, Brosamle 2000), Nogo receptor antagonist peptide NEP1-40 (GrandPré 2002) and truncated soluble Nogo receptor (Fournier 2002). More recently, researchers have generated different Nogo knockout mice models, with conflicting results as to an increase in regenerative capacity (Simonen 2003, Zheng 2003, Kim 2003). Other groups have sought to increase neurite regrowth by inducing an immune response against myelin-associated axonal regrowth inhibitors (Huang 1999), or specifically against Nogo-A derived peptide 472 (Hauben 2001), with a moderate degree of success that was attributed to the generation of an antibody response against non-descriminated myelin components or to a T-cell specific response against p472.

Experimental autoimmune encephalomyelitis (EAE) is an animal model that has been intensely investigated as a source of pathophysiological and therapeutic insight into the human disease multiple sclerosis (MS) (Steinman 2002, Steinman 1999). EAE is mainly mediated by a myelin-antigen specific T cell response that coordinates the immune attack against the CNS (Steinman and Zamvil 1990). The role of the B cell response is not as clear in EAE and MS, although antibodies targeting myelin oligodendrocyte glycoprotein (MOG) are thought to be pathogenic in both EAE and MS, and other anti-myelin antibodies have been detected (Genain 1999, Steinman 1996). Epitope spreading of the B cell response occurs after active EAE induction and its presence correlates with relapse rate in chronic models. In recent years, axonal pathology has also emerged as a major determinant of neurological deficit in MS (Trapp 1998), leading to the belief that blocking the action of axonal regrowth inhibitors might also be beneficial in this disease.

It is an object of the present invention to provide a method of treating or preventing a demyelinating disease. Another object of this invention is to provide a specific method for treating or preventing autoimmune diseases that does not impair the immune system generally. These and other objects of this invention will be apparent from the specification as a whole.

SUMMARY OF THE INVENTION

Compositions and methods are provided for the use of Nogo epitopic fragments, in particular Nogo peptides, in the diagnosis and treatment of autoimmune disease. It was the discovery of this invention that administration of Nogo epitopic fragment(s), particularly Nogo peptide 45-66 modulates an immune response in a demyelinating autoimmune disease. Nogo epitopic fragments are useful therapeutically in the generation of a protective immune response for inflammatory central nervous system disease. Nogo epitopes may be administered as peptides, DNA vaccines, and the like. Fragments of Nogo that provide for protective immune responses are of particular interest, and include, without limitation, peptides present in the extracellular 66-amino acid loop of Nogo-A protein.

DETAILED DESCRIPTION OF THE EMBODIMENTS

A specific and strong T cell response, and a B cell response, can be generated against Nogo peptides, which does not cross-react to other myelin antigens. T cells reactive to Nogo antigens are capable of ameliorating ongoing disease, which may be induced with other antigens. The present invention provides compositions and methods for the identification and use of Nogo epitopic fragments in the treatment of immune related disease. Diseases of interest include inflammatory central nervous system disease, e.g. EAE, multiple sclerosis (MS), etc.

In one aspect of the invention, an autoantigen specificity profile is generated for a patient with an autoimmune disease, by contacting a patient sample comprising an antigen specific immunological agent with Nogo or a Nogo epitopic fragment derived therefrom; and identifying the presence of binding or reactivity between Nogo or the Nogo epitopic fragment and the immunological agent. In one embodiment of the invention, the patient sample is contacted with an array of autoantigens comprising Nogo or Nogo epitopic fragment(s), which may further comprise additional autoantigens, particularly other myelin antigens, e.g. myelin associated glycoprotein (MAG), proteolipid protein (PLP), myelin-basic protein (MBP), myelin oligodendrocyte glycoprotein (MOG), oligodendrocyte-specific glycoprotein (OSP), 2',3'-cyclic nucleotide 3'-phosphodiesterase (CPNase) and alpha-B crystallin. In another embodiment, the autoantigen or array of autoantigens is provided in the form of a multimer comprising MHC-antigen complexes, which multimer binds to T cells with sufficient avidity to permit specific binding to the cognate T cell antigen receptor. The patient sample may comprise autoantibodies as the immunological agent. Alternatively the patient sample may comprise T cells as the immunological agent. In one embodiment, a high throughput determination is made of the spectrum of disease relevant antibodies present in patient serum by detailed binding analyses.

In another embodiment of the invention, Nogo or Nogo epitopic fragments derived therefrom is used to immunize or treat a patient suffering from or at risk of developing, an inflammatory central nervous system disease. The Nogo epitopic fragment may be presented as a peptide, an altered peptide, a nucleic acid encoding a peptide, or the like. The Nogo epitopic fragment may be administered in combination with a second Immunomodulatory agent.

In certain embodiments of the invention, the second immunomodulatory agent is antigen specific. In one embodiment, the antigen-specific immunomodulatory agent is a self-vector that includes a polynucleotide encoding a self-polypeptide associated with the autoimmune disease. The self-polypeptide encoded by the polynucleotide can be, for example, a protein or a peptide. In certain embodiments, the self-vector comprising a polynucleotide encodes one self-polypeptide.

In another embodiment, the antigen-specific immunomodulatory agent is a polypeptide. The polypeptide can be, for example, a protein or a peptide. In addition, the polypeptide can include a self-polypeptide associated with the disease or can include amino acids corresponding to an autoantigenic epitope of a self-polypeptide associated with the disease. In embodiments where the polypeptide includes amino acids corresponding to an autoantigenic epitope, the amino acids can be randomized to form a random copolymer or ordered such that the polypeptide includes an ordered amino acid motif. In one embodiment where the autoimmune disease is a demyelinating autoimmune disease, the ordered amino acid motif is $[^1E^2Y^3Y^4 K]_n$, where n is from 2 to 6. (SEQ ID NO:1).

In other embodiments, the second immunomodulatory agent is non-antigen-specific. In one embodiment, the non-antigen specific immunomodulatory agent is osteopontin or a self-vector comprising a polynucleotide encoding osteopontin. In other embodiments, the non-antigen specific immunomodulatory agent is an immune modulatory sequence. The immune modulatory sequence can be, for example, 5'-Purine-Pyrimidine-[X]-[Y]-Pyrimidine-Pyrimidine-3' or 5'-Purine-Purine [X]-[Y]-Pyrimidine-Pyrimidine-3', where X and Y are any naturally occurring or synthetic nucleotide, except that X and Y cannot be cytosine-guanine.

In other embodiments, the non-antigen specific immunomodulatory-agent is a statin that is administered after the initial onset of the autoimmune disease. The statin can be, for example, rosuvastatin, mevastatin, lovastatin, pravastatin, simvastatin, fluvastatin, atorvastatin, or cerivastatin.

Without being limited to the mechanisms by which the methods of the invention operate, it is believed that T cells reactive against Nogo epitopic fragments migrate to inflammatory sites and cross-regulate other myelin reactive cells by adopting beneficial Th2 phenotypes.

Nogo-A is a member of the reticulon family of proteins. The genetic and amino acid sequence may be found at Genbank, accession number AF148537. Nogo has two inhibitory domains, a cell surface domain called Nogo-66 (see GrandPre et al. (2000) *Nature* 403:439), and a long amino terminal region. The Nogo-66 domain binds to NgR. In the methods of the present invention, a Nogo epitopic fragment, such as a Nogo polypeptide or peptide fragment thereof or polynucleotide encoding such a polypeptide or peptide fragment thereof may be used.

In the present specification and claims, the terms "polypeptide fragments," "Nogo polypeptide fraqment," "peptide fragment," "Nogo peptide fragment," or "polypeptide or peptide fragment," or variants thereof, denotes both short peptides with a length of at least two amino acid residues and at most 10 amino acid residues, oligopeptides with a length of at least 11 amino acid residues, 20 amino acid residues, 50 amino acid residues, and up to about 100 amino acid residues; and longer peptides of up to about 200 amino acid residues.

The term substantially pure polypeptide or peptide fragment means a polypeptide or peptide preparation which contains at most 5% by weight of other polypeptide or peptide material with which it is natively associated, and lower percentages are preferred, e.g. at most 4%, at most 3%, at most 2%, at most 1%, and at most 0.5%. It is preferred that the substantially pure polypeptide or peptide is at least 96% pure, i.e. that the polypeptide or peptide constitutes at least 96% by weight of total polypeptide or peptide material present in the preparation, and higher percentages are preferred, such as at least 97%, at least 98%, at least 99%, at least 99.25%, at least 99.5%, and at least 99.75%. It is especially preferred that the polypeptide or peptide fragment is essentially free of any other antigen with which it is natively associated. This can be accomplished by preparing the polypeptide or peptide fragment by means of recombinant methods, or by synthesizing the polypeptide or peptide fragment by the well-known methods of solid or liquid phase peptide synthesis, e.g. by the method described by Merrifield or variations thereof.

The Nogo antigens or Nogo fragments, such as Nogo epitopic polypeptides or peptides, provided herein include variants that are encoded by DNA sequences that are substantially homologous to one or more of the DNA sequences specifically recited herein, for example variants having at least 80%, 85%, 90%, 91%, 92%, 93%, 94%, 95%, 96%, 97%, 98%, 99%, or 99.5% sequence identity.

In a preferred embodiment of the invention, polypeptide or peptide fragments provide for or encompass an epitope. The binding site of antibodies typically utilizes multiple non-covalent interactions to achieve high affinity binding. While a few contact residues of the antigen may be brought into close proximity to the binding pocket, other parts of the antigen molecule can also be required for maintaining a conformation that permits binding. The portion of the antigen bound by the antibody is referred to as an epitope. As used herein, an epitope is that portion of the antigen that is sufficient for high affinity binding. In a polypeptide or peptide antigen, generally a linear epitope will be at least about 7 amino acids in length, and may be at least 8, at least 9, at least 10, at least 11, at least 12, at least 14, at least 16, at least 18, at least 20, at least 22, at least 24, or at least 30 amino acid residues in length. However, antibodies may also recognize conformational determinants formed by non-contiguous residues on an antigen, and an epitope can therefore require a larger fragment of the antigen to be present for binding, e.g. a domain, or up to nearly substantially all of a protein sequence. For each antigen there exists a plurality of epitopes that, in sum, represent the immunologic determinants of that antigen, although there are instances in which an antigen contains a single epitope.

The level of affinity of antibody binding that is considered to be "specific" will be determined in part by the class of antibody, e.g. antigen specific antibodies of the IgM class may have a lower affinity than antibodies of, for example, the IgG classes. As used herein, in order to consider an antibody interaction to be "specific", the affinity will be at least about $10^{-7}$ M, usually about $10^{-8\ to\ -9}$ M, and may be up to $10^{-11}$ or higher for the epitope of interest. It will be understood by those of skill in the art that the term uspecificityn refers to such a high affinity binding, and is not intended to mean that the antibody cannot bind to other molecules as well. One may find cross-reactivity with different epitopes, due, e.g. to a relatedness of antigen sequence or structure, or to the structure of the antibody binding pocket itself. Antibodies demonstrating such cross-reactivity are still considered specific for the purposes of the present invention.

Polypeptide or peptide sequences include analogs and variants produced by recombinant methods wherein such nucleic acids and polypeptide or peptide sequences are modified by substitution, insertion, addition, and/or deletion of one or more nucleotides in the nucleic acid sequence to cause the substitution, insertion, addition, and/or deletion of one or more amino acid residues in the recombinant polypeptide.

Specific polypeptides or peptides and analogs thereof of this invention may be administered therapeutically to induce tolerance or a protective T cell response to treat autoimmunity. Native polypeptides or peptides of this invention targeted by the autoimmune response can be delivered to induce tolerance or a protective T cell response. Delivery of polypeptides or peptides that are altered from the native peptide may also be used. Alteration of native polypeptides or peptides with selective changes of residues (altered peptide ligands or "APL") can induce unresponsiveness or change the responsiveness of antigen-specific autoreactive T cells.

"Peptide analogs" are at least seven amino acids in length and contain at least one difference in amino acid sequence between the analog and native antigenic peptide. An L-amino acid from the native peptide may be altered to any other one of the 20 L-amino acids commonly found in proteins, any one of the corresponding D-amino acids, rare amino acids, such as 4-hydroxyproline, and hydroxylysine, or a non-protein amino acid, such as β-alanine and homoserine. Also included with the scope of the present invention are amino acids that have been altered by chemical means such as methylation (e.g., α-methylvaline), deamidation, amidation of the C-terminal amino acid by an alkylamine such as ethylamine, ethanolamine, and ethylene diamine, and acylation or methylation of an amino acid side chain function (e.g., acylation of the epsilon amino group of lysine), deimination of arginine to citrulline, isoaspartylation, or phosphorylation on serine, threonine, tyrosine or histidine residues.

The mechanism of action of how altered peptide ligands are efficacious may involve incomplete mobilization of the T cell receptor (TCR). There are several possible functional alterations that the APL can induce. The first is as a simple antagonist, where the APL may compete for MHC binding with the native peptide on the antigen presenting cell and not allow for complete T cell activation. This implies that there is no signal transmitted through the T cell receptor by the APL. The second is by anergy, where the APL induces a state of complete nonresponsiveness in the T cell such that the T cell does not respond to the native peptide. The third is by phenotypic switching, where the APL may induce a functional switch in the T cell such that it decreases the production of proinflammatory cytokines and/or increase the production of noninflammatory cytokines such as IL-4 or IL-10.

A candidate polypeptide or peptide analogs may be screened for their ability to treat disease by an assay measuring competitive binding to MHC, and an assay measuring T cell proliferation. Those analogs that inhibit binding of the native polypeptide or peptides and do not stimulate proliferation of auto-reactive T cells are useful therapeutics. A candidate polypeptide or peptide analog(s) are further tested for their property of stimulating or inhibiting proliferation of T cells, by measuring the ability of the analog to cause proliferation of T cells in a direct fashion, and by determining the response profile of the T cells thus induced, i.e. by determining whether a T cell has a suppressive or a pro-inflammatory profile.

Nogo epitopic fragments of interest include, without limitation, Nogo 1-22; Nogo 23-44; and Nogo 45-66; particularly Nogo 45-66, or a portion thereof, wherein said portion thereof is sufficient to induce a protective immune response. In this invention, the extracellular 66-amino acid loop in the C-terminus end was numbered from 1 to 66. One of ordinary skill in the art will be able to identify the corresponding numbering of the extracellular 66 amino acid loop for the three isoforms of Nogo protein as set forth in Genbank. One Nogo epitopic peptide of this invention is Nogo45-66 having the sequence: VNSTIKELRRLFLVDDLVDSLK (SEQ ID NO:2). Another Nogo epitopic peptide of this invention is Nogo45-66 having the sequence: VNCTIKELRRLFLVDDLVDSLK (SEQ ID NO:3).

Specificity analysis of patient reactivity. In one aspect of the invention, an autoantigen specificity profile is generated for a patient with an autoimmune disease, by contacting a patient sample comprising an antigen specific immunological agent with at least one Nogo polypeptide or peptide or an epitopic fragment derived therefrom; and identifying the presence of binding or reactivity between the Nogo epitopic fragment and the immunological agent. In one embodiment of the invention, the patient sample is contacted with an array of autoantigens comprising at least one Nogo polypeptide or peptide. In another embodiment, the autoantigen or array of autoantigens is provided in the form of a multimer comprising MHC-antigen complexes, which multimer binds to T cells with sufficient avidity to permit specific binding to the cognate T cell antigen receptor. The patient sample may comprise autoantibodies as the immunological agent. Alternatively the patient sample may comprise T cells as the Immunological agent. In one embodiment, a high throughput determination is made of the spectrum of disease relevant antibodies present in patient serum by detailed binding analyses.

Formats for human patient sampling include time courses that follow the progression of disease, comparisons of different patients at similar disease stages, e.g. early onset, acute stages, recovery stages, etc.; tracking a patient during the course of response to therapy, including drug therapy, vaccination and the like. Data from animals, e.g. mouse, rat, rabbit, monkey, etc. may be compiled and analyzed in order to provide databases detailing the course of disease, antigens involved in diseases, etc.

Biological samples from which patient antibodies may be collected include blood and derivatives therefrom, e.g. serum, plasma, fractions of plasma, etc. Other sources of samples are body fluids such as synovial fluid, lymph, cerebrospinal fluid, bronchial aspirates, and may further include saliva, milk, urine, and the like. Both antibodies and T cell receptors may also be obtained from the appropriate lymphocytes, which may be collected from blood, tissues such as spleen, thymus, lymph nodes, fetal liver, tissues at the site of autoimmune lesions, e.g. pancreas, joints, kidneys, cerebrospinal fluid, etc. The lymphocytes may be analyzed intact, or lysates may be prepared for analysis. Patient samples contain antibodies, and binding to Nogo can be used to profile these antibodies.

In a typical assay, a patient sample containing antibodies or T cells is physically contacted with the antigen, under conditions that permit high affinity binding, but that minimize non-specific interactions. The means for identifying the disease-associated antigens that bind to the antibodies within the patient sample utilize methods for detection that are known in the art. Those methods of identification may include prelabeling the sample directly or indirectly; adding a second stage antibody that binds to the antibodies or to an indirect label, e.g. labeled goat anti-human serum, rat anti-mouse, and the like. Other methods of identification include analysis of addressable elements on an array such as beads, nanoparticles, tags, cleavable tags and other physical properties of or conferred upon the elements. Varying concentrations of a single epitope may be present in order to facilitate quantitation of the bound antibody.

Useful labels include fluorochromes, e.g. Cy2, Cy3, Cy5, fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4', 7',4,7-hexachlorofluorescein (HEX), 5-carboxyfluorescein (5-FAM) or N N,N',N'-tetramethyl-6-carboxyrhodamine (TAMRA)). Indirect labels include haptens, such as digoxin and digoxigenin, biotin, etc., where a second stage binding partner, e.g. avidin, anti-digoxin antibody, etc., may be labeled with an enzyme, e.g. horseradish peroxidase, fluorochrome, radioactive label, etc. Preferably, where a control sample is included, the fluorescent reporter used to label the control sequences emits a fluorescent signal at an excitation and/or emission wavelength detectably distinct from that of the fluorescent reporter used to label the test sequence.

Detection may also occur using methods that do not require labeling. Examples include detection of changes in charge or mass of the bound self-antigen using methods or devices such as single electron transistors, proteins applied to carbon nanotubes or meshworks of nanotubes, surface plasmon resonance, atomic force microscopy, and other methods known to those skilled in the art.

Generally assays will include various negative and positive controls, as known in the art. These may include positive controls of "spiked" samples with known autoantibodies, patients with known disease, and the like. Negative controls include samples from normal patients, animal serum, and the like.

Binding of the antibody containing sample to an antigen is accomplished according to methods well known in the art. The binding conditions and washes are preferably carried out under conditions that allow only high affinity binding partners to be retained.

Two-color labeling of different antibodies can be utilized in binding to the same or to separate samples, in order to assay the level of binding in a patient sample compared to a control sample. From the ratio of one color to the other, for any antigen, the relative abundance of antibodies with a particular specificity in the two samples can be determined. In addition, comparison of the binding of the two samples provides an internal control for the assay. Competitive assays are well known in the art, where a competing antibody of known specificity, or an epitope containing molecule, may be included in the binding reaction.

Various methods may be used to determine the autoantigen specificity profile from a patient sample. An autoantigen specificity profile is initially determined for an individual patient, and as used herein means the autoantigens or epitopes that are bound by the antibodies and/or T cells from a patient sample. The comparison of a binding pattern obtained from a patient sample and a binding pattern obtained from a control, or reference, sample is accomplished by the use of suitable deduction protocols, AI systems, statistical comparisons, pattern recognition algorithms, etc. The information from reference patterns can be used in analytical methods to determine induction, antigen or epitope spreading, relative abundance, changes over time, changes in antibody isotype produced, and other related changes.

Once the subset of specificities for a particular sample are identified, the data may be used in developing new diagnostic agents, and in selecting the most appropriate therapy for an individual. By analysis of autoantibody specificity on an individual basis, the specific epitope targets that are present in the disease state are determined. One or more therapeutic agents can then be selected, which have the best specificity for the individual patient and disease.

Therapeutic Methods The term "treatment" or "treating" means any treatment of a disease in a mammal, including autoimmune diseases in human, and animals. Treatment includes preventing the disease, that is, causing the clinical symptoms of the disease not to develop by administration of a Nogo epitopic fragment composition prior to the induction of the disease; suppressing the disease, that is, causing the clinical symptoms of the disease not to develop by administration of a Nogo epitopic fragment composition after the inductive event but prior to the clinical appearance or reappearance of the disease; inhibiting the disease, that is, arresting the development of clinical symptoms by administration of a Nogo epitopic fragment composition after their initial appearance; and/or relieving the disease, that is, causing the regression of clinical symptoms by administration of a Nogo epitopic fragment composition after their initial appearance.

It will be understood that in human medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "treatment," as used herein, is meant to include "prophylaxis."

The term "effective amount" means a dosage sufficient to provide treatment for the disease state being treated. This will vary depending on the patent, the disease and the treatment being effected. In vivo activity may be demonstrated by testing in an animal model for abnormal B and T cell function mimicking the human situation, in control and treated groups. Human clinical efficacy is demonstrated in clinical trials, employing methodology known to those skilled in the art.

Various methods for administration may be employed. The dosage of the therapeutic formulation comprising a Nogo epitopic fragment will vary widely, depending upon the nature of the disease, the frequency of administration, the manner of administration, the purpose of the administration, the clearance of the Nogo epitopic fragment from the host, and the like. The dosage administered will vary depending on known factors, such as the pharmacodynamic characteristics of the particular Nogo epitopic fragment, mode and route of administration, age, health and weight of the recipient, nature and extent of symptoms, concurrent treatments, frequency of treatment and effect desired. The dose may be administered as infrequently as weekly, biweekly or monthly or fractionated into smaller doses and administered daily, semi-weekly, etc. to maintain an effective dosage level. Generally, a daily dosage of active Nogo epitopic fragment can be about 0.01 to 100 mg/kg of body weight. Dosage forms suitable for internal administration generally contain from about 0.1 mg to 500 mgs of active Nogo epitopic fragment per unit. The active Nogo epitopic fragment may vary from 0.5 to 95% by weight based on the total weight of the composition.

Nogo epitopic fragment(s) or variants thereof can be utilized to develop and select antigen or epitope specific therapies, which comprise administration of a Nogo epitopic fragment and an antigen or epitope specific therapeutic agent. Therapeutic methods include but are not limited to: oral administration of specific-antigens, termed 'oral tolerance' (Annu Rev Immunol. 12:809-37); administration of native peptides (Science 258:1491-4; J Neurol Sci, 152:31-8); administration of altered peptide ligands (Nature 379:343-5); administration of whole proteins (Science 263:1139); administration of fusion-proteins or peptides; and administration of polynucleotide sequences encoding the targeted self-proteins or allergens (J. Immunol. 162:3336-41; Curr. Dir. Autoimmun. 2:203-16). For all of these therapies, the antigens administered (or encoded in DNA) for purposes of immune suppression may comprise all or a portion of the epitopes identified by antibody or T cell receptor. In one embodiment, one or more of the epitopes thus identified are administered, usually two or more, more usually three or more, and may comprise as many as ten or more different epitopes. Individual peptides or DNA encoding peptides may be administered. Alternatively, whole proteins, or DNA encoding all or substantially all of the antigenic protein may be administered. One or more, usually two or more, and as many as three of more different protein antigens may be thus administered. Antigen-specific therapy as used herein refers to a therapeutic regimen based upon an antigen specificity profile determined by the novel method of this invention.

In one embodiment, treatment comprises administration of a Nogo epitopic fragment in combination with the administration of a DNA expression cassette injected into host tissue, for example muscle or skin, or administration of peptides to induce an antigen-specific, suppressive T-cell response, for example as described in PCT application US00/0623; US02/37686; and WO 02/084249, herein incorporated by reference. The vector comprises a DNA sequence encoding at least a portion of an autoantigen, transplant antigen, etc. In response to this vaccination, a suppressive response is evoked. Antigen-specific T cell proliferation is inhibited and Th1 cytokine production is reduced. The therapeutic composition comprising a Nogo epitopic fragment may be formulated with DNA encoding one epitope or a cocktail of epitope sequences. It may be desirable in some cases to include multiple sequences, where each encodes a different epitope. For example, see Leadbetter et al. (1998) J. Immunol. 161:504-512. A formulation comprised of multiple coding sequences of distinct epitopes may be used to induce a more potent and/or sustained suppressive response. By specifically targeting multiple autoreactive T cell populations, such a formulation may slow or prevent the development of autoantigen resistance.

The prevention of autoimmune disease involving a targeted antigen is accomplished by administration of the Nogo epitopic fragment prior to development of overt disease. The treatment of ongoing disease, where the Nogo epitopic fragment stabilizes or improves the clinical symptoms of the patient, is of particular interest. Such treatment is desirably performed prior to complete loss of function in the affected tissues.

EXPERIMENTAL

Example 1

Figure 1:
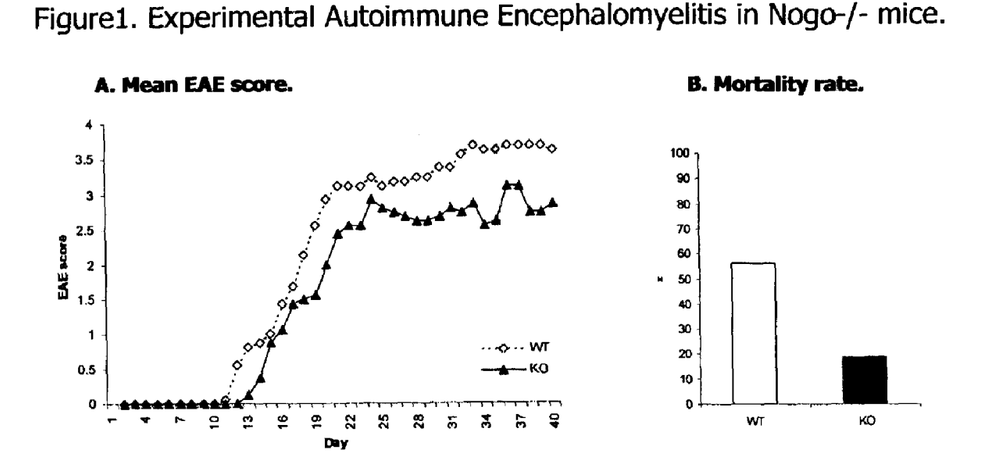
FIG. 1A. Nogo KO mice have a non-statistically significant reduction in disease severity compared to wild-type C57BL/6 controls.
FIG. 1B. Nogo KO mice have a reduction in mortality rate (FIG. 1B).

Induction of EAE in Nogo A/B/C mutant mice. In order to study the possible contribution of the Nogo-A protein to axonal regeneration in the EAE model, we induced disease in Nogo-A/B/C knockout mice (C57BU6 by 129S background) generated by targeted mutation of the common C-terminal region that contains Nogo-66 (Zheng 2003), using subcutaneous injection of 100 µg of MOG35-55 peptide emulsified in complete Freunds adjuvant (CFA) and intravenous pertussis toxin. Animals were followed for 6 weeks post-induction for disease phenotype. As shown in FIG. 1A, Nogo KO mice show no difference in disease severity (not statistically significant) compared to wild-type C57BU6 controls, which is mainly attributable to a reduction in mortality rate (FIG. 1B). Histological evaluation at the end of the experiment by standard myelin staining did not reveal an appreciable difference in lesion type or severity, or in the presence of axonal pathology as demonstrated by axonal staining. Nogo-66 may have a specific role as a modulatory autoantigen capable of modifying disease course in EAE.

Induction of EAE and T cell responses with Nogo-66 peptides in susceptible mouse strains. To ascertain the potential for Nogo-A to act as a target autoantigen for autoimmune demyelination, we chose to focus on the exposed extracellular 66-amino acid loop, Nogo-66, since this should be the region most prone to interaction with immune cells. EAE susceptible SJL/J and C57BU6 female mice of the appropriate age were subcutaneously immunized with Nogo-66 derived peptides in CFA, in various concentration ranging from 200 µg to 1000 µg, together with intravenous administration of Pertussis toxin.

Figure 2:
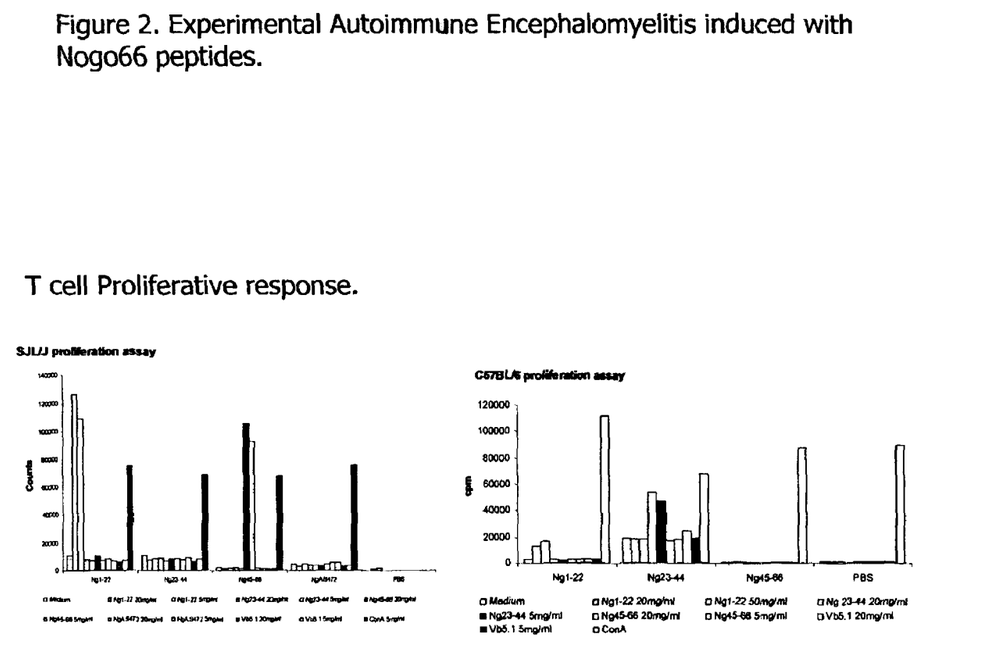
FIG. 2. Evaluation of T cell proliferative response against immunizing antigen.

Three different arbitrarily selected peptides were synthesized to encompass the whole sequence (peptides 1-22, 23-44 and 45-66). Histological evaluation of the brain and spinal cord of select Nogo-immunized animals revealed the presence of inflammation in the meninges and parenchyma. To evaluate the generation of a T cell proliferative response against the immunizing antigen, we collected draining lymph nodes at the end of the experiments and setup whole lymph node cell proliferation assays against our panel of Nogo and irrelevant peptides. We found a strong and specific proliferative response against pNogo1-22 and pNogo45-66 in SJL/J animals, and to a lesser degree to pNogo1-22 and pNogo23-44 in C57BU6 animals (FIG. 2). Therefore, T cell epitopes appear to be slightly different between these two strains.

Nogo-66 peptide immunization induces a B cell response with epitope spreading to other myelin antigens. To follow the induction of a specific antibody response to the immunizing Nogo peptides, and the possible spread to other myelin antigens, we used an 2304-feature spotted peptide array developed in our laboratory that contains 293 distinct antigens including proteins and sets of overlapping peptides representing all major EAE-relevant targets and several Nogo-66 overlapping peptides together with p472 (Robinson, 2001). Sera from several immunized animals was obtained at different time points after EAE induction with all three Nogo peptides, and hybridized to the proteome array according to our protocol. Results show that after immunization with each Nogo-66 peptide, a strong and specific B cell response occurs to the immunizing antigen in both strains (FIGS. 3A and 3B).

Figure 3:
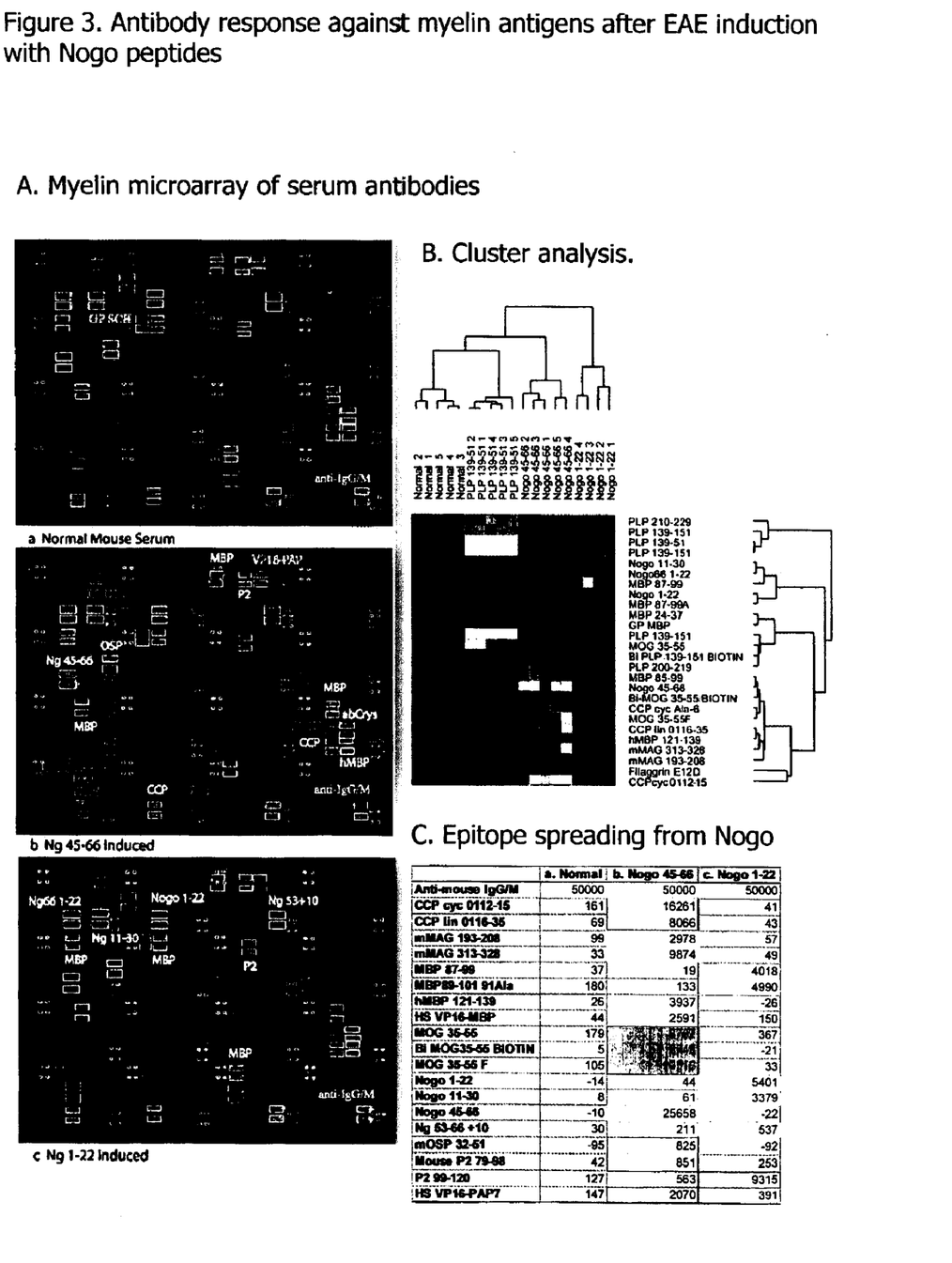
FIGS. 3A and 3B. Results after immunization with Nogo-66 peptide.
FIG. 3C. Intra and intermolecular epitope spreading of the antibody response to other myelin peptides and proteins.

Statistical and cluster analysis of array data from several grouped animals also revealed marked intra and intermolecular epitope spreading of the antibody response to other myelin peptides and proteins, such as MAG (p193-208, p313-328), PLP (p1-19, p10-29, p103-116, p139-151, p150-169), MBP (p85-99, p121-139, p131-149, p139-151, p151-170, VP16-MBP), MOG (p1-26, p35-55, p162-178), OSP (p32-51, p172-191), alpha-B Crystallin (p121-140), CNPase (p343-373) and Nogo (p31-52, p11-30) (FIG. 3C). This was particularly relevant after immunization with pNogo45-66 in both strains, and with pNogo23-44 for C57BU6 mice. Spreading of the B cell response evidenced a specific pattern for each immunizing antigen within each strain, with very little overlap between them. The B cell response spreads from pNogo1-22 mainly to MBP peptides, from pNg23-44 to MOG and MBP peptides (especially in C57BU6 animals) and from pNogo45-66 to MAG, MBP, PLP, OSP and alpha-B Crystallin (FIG. 3C). Therefore, our results show that pNogo45-66 is a much stronger B cell antigen than any of the other two synthesized peptides.

Figure 4:
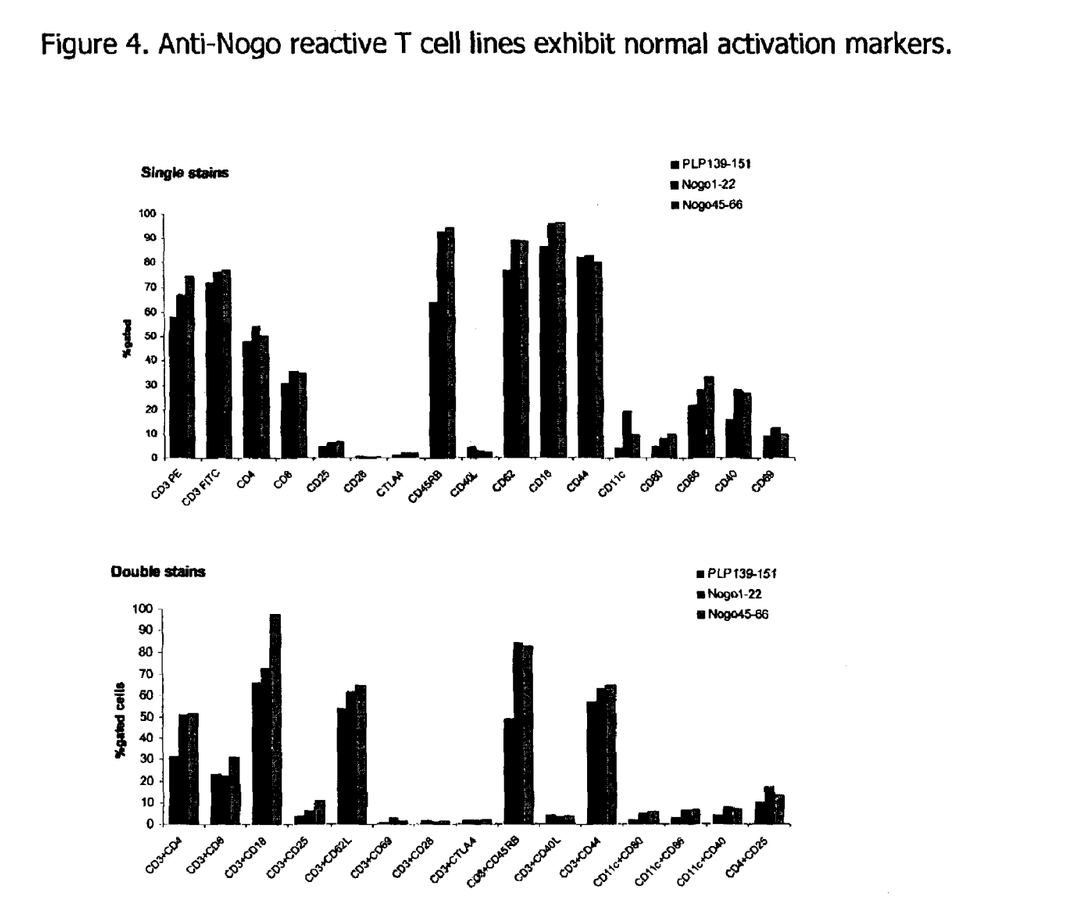
FIG. 4. Nogo immunization generates a specific T cell response that does not show cross-reactivity to other myelin autoantigens.

The T cell response to Nogo-66 peptides is specific and does not cross react with other myelin antigens. We tested the specificity of the T cell response by evaluating the cross reactivity between Nogo peptides and PLP139-151 or MOG35-55, which are known myelin autoantigens. In order to do so, we created anti-pNogo1-22, anti-pNogo45-66 and anti-PLP13-151 specific T cell lines from SJL/J animals immunized with these peptides, and studied their in vitro proliferation against several myelin antigens. As can be seen (FIG. 4), a T-cell line specific for PLP139-151 actively proliferates against its cogent antigen, but shows no reactivity to all three Nogo-66 peptides. Nogo-peptide generated T cell lines also show reactivity only against their specific peptide, and do not proliferate against PLP139-151, MBP85-99 or MOG35-55. Therefore, we conclude that Nogo immunization generates a specific T cell response that does not show cross-reactivity to other myelin autoantigens. Since the secondary structure of the Nogo protein is currently not known, we compared the primary structure of the Nogo peptides with the ones for PLP139-151 and MOG35-55 using computer modeling and well known primary structure scales for hydropathicity (Kyte and Doolitle), polarity (Zimmerman), recognition factors and bulkiness. Using these measures, we could not find any relevant comparisons between Nogo-66 peptides and the other studied myelin antigens (FIG. 4). Analysis of the full length Nogo-66 sequence for potential immunogenic domains, based on the aforementioned primary structure scales, appears to indicate the existence of regions of increased probability within the sequence of each of the peptides arbitrarily selected for immunization in our experiments.

Figure 5:
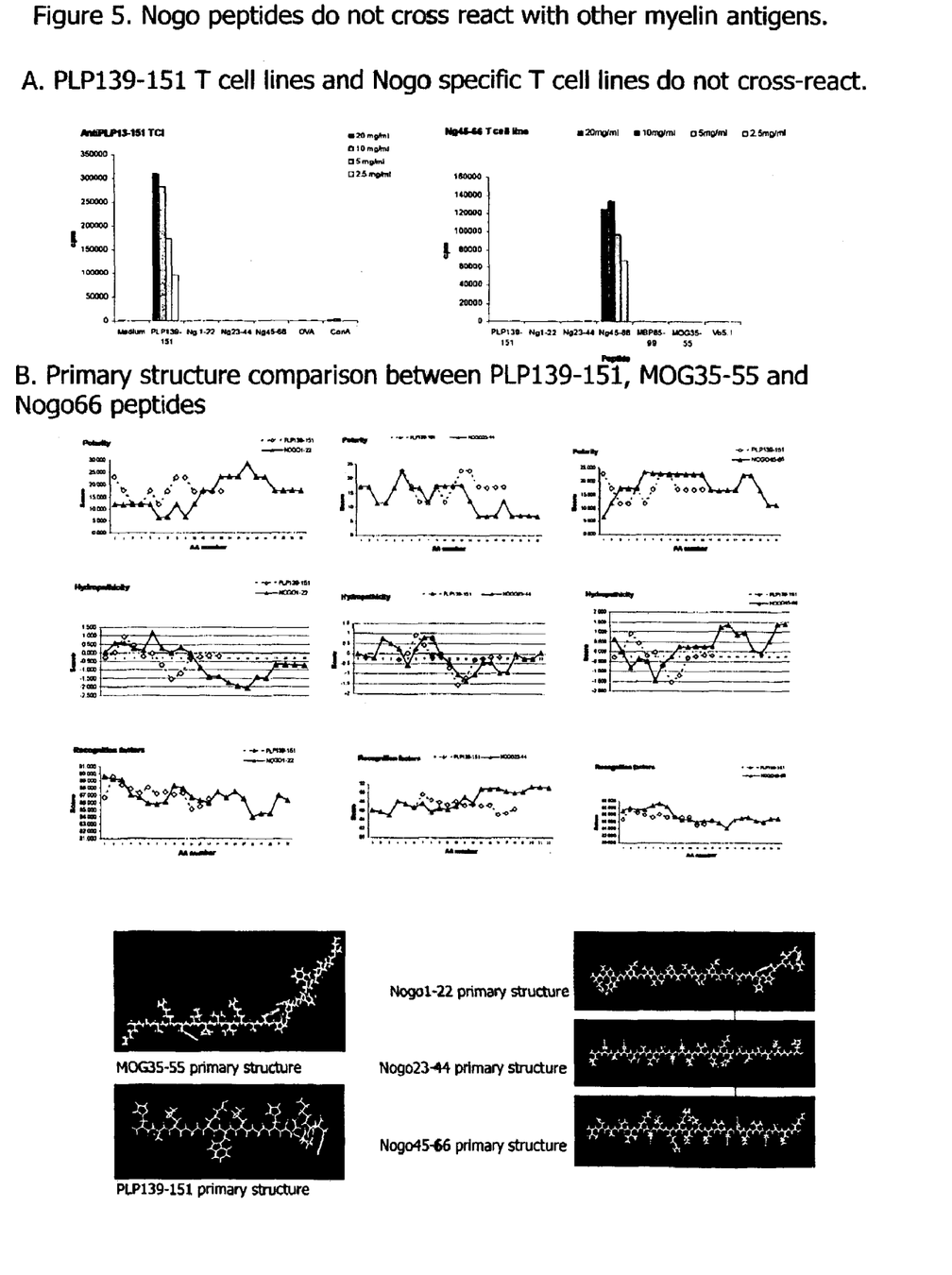
FIG. 5A-5B. Cell surface expression of CD25, CD18, CD40L, CD62, CD69, CD28 and CTLA4e in T cells or CD80, CD86, CD40 in dendritic cells does not differ between Nogo immunized animals and animals immunized with other myelin antigens.

Nogo-peptide reactive T cells exhibit a normal activation phenotype. We purified whole lymph node cells from female SJL/J animals 10 days post-immunization with PLP139-151, pNogo1-22 and pNogo45-66 and looked at the expression of several activation markers and co-stimulatory molecules by fluorescence activated cell scan (FACScan) analysis. Overall, we could not find any difference in cell surface expression of CD25, CD18, CD40L, CD62, CD69, CD28 and CTLA4e in T cells or CD80, CD86, CD40 in dendritic cells (FIGS. 5A and 5B). Nogo-peptides are capable of normal presentation by APC and immunization leads to normal activation of T cells.

Adoptive transfer of anti-Nogo reactive T cell lines ameliorates EAE in SJL/J mice. We next attempted to induce disease in SJL/J female mice by adoptive transfer of anti-Nogo T cell lines. In order to do so, naive mice were immunized with pNogo1-22 or pNogo45-66 emulsified in CFA and 10 days later, draining lymph nodes were collected, whole lymph node cell culture were purified and restimulated in vitro with the Nogo peptide. From these we established antigen-specific T cell lines (TCL), which were used for adoptive transfer and cytokine secretion profile evaluation.

Figure 6:
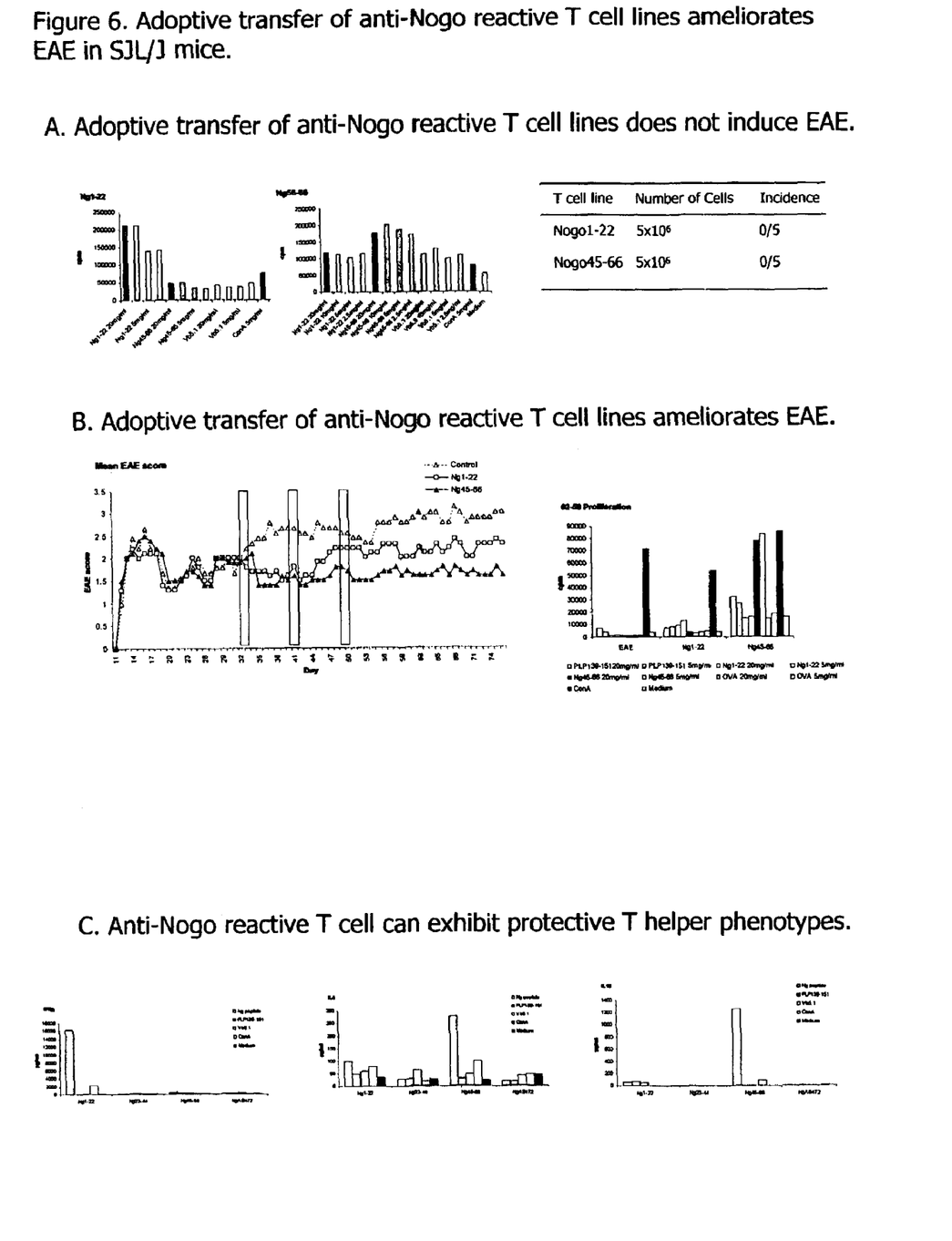
FIG. 6A. Animals were immunized with Nogo epitopic fragments, particularly Nogo peptides, pNogo1-22 or pNogo45-66 and antigen specific T cell lines (TCL) were established for adoptive transfer. SJL mice receiving Nogo-reactive TCL did not induce EAE.
FIG. 6B. EAE was induced in SJL/J mice by immunization with PLP139-151. At the peak of the second relapse animals received either PBS, anti-pNogo1-22 or anti-pNogo4566 reactive T cells by intravenous administration. Animals receiving Nogo-reactive T cells showed a statistically significant reduction in clinical score, particularly those receiving anti-pNogo45-66 TCL. In vitro proliferation assays demonstrate the existence of both PLP139-151 and Nogo reactive T cells.
FIG. 6C. The phenotype of anti-Nogo TCL was examined by in vitro cytokine production assays. Anti-Nogo1-22 and anti-Nogo45-66 TCL were stimulated in vitro with their specific antigen in the presence of syngeneic irradiated antigen presenting cells. Supernatants were collected and cytokine production measured by ELISA. Anti-pNogo45-66 TCL developed a Th2 phenotype, producing large amounts of IL4 and IL-10, whereas anti-pNogo1-22 TCL showed increased production of IFNγ.

We transferred up to 50 million TCL reactive against pNogo1-22 or pNogo45-66 intravenously into naive SJL mice, which were followed for clinical signs of disease. In one of the experiments, animals received 10 million TCL and were boosted 15 days later with 100 μg of Nogo-peptide emulsion in CFA and intravenous pertussis toxin injection. Although we could demonstrate the presence of Nogo reactive T cells in adoptively transferred animals up to 2 months later by in vitro proliferative responses, these animals never developed clinical signs of disease (FIG. 6A). Given that Nogo-66 is a minor component of myelin and thus possibly a hidden autoantigen, this inefficiency at disease induction might be overcome by transferring Nogo-reactive cells into already diseased animals, in which Nogo-66 might be available for presentation to T cells in acute demyelinating foci.

We induced EAE in SJL/J mice by immunization with 100 μg of PLP139-151 peptide in CFA and followed these animals for disease course. At the peak of second relapse (day 31), animals were randomized into three groups and received either weekly PBS, anti-pNogo1-22 or anti-pNogo45-66 reactive T cells in PBS (average of 15 million cells), by intravenous administration for three weeks. Four days after TCL transfer, animals receiving Nogo-reactive TCL showed a statistically significant reduction in clinical score (Mann-Whitney $p<0.05$), especially the ones receiving anti-pNogo45-66 TCL (FIG. 6B). For these animals, this improvement was maintained throughout the next 45 days of the experiment, up to 30 days after the last TCL administration. For anti-pNogo1-22 the effect was more transient, and clinical scores worsened after the last administration, but not to PBS control levels. At the end of the experiment, we could still demonstrate by in vitro proliferation assays the existence of both PLP139-151 and Nogo reactive T cells (FIG. 6B). In fact, proliferation against pNogo45-66 was much stronger than against the EAE inducing antigen, suggesting that there might be cross-suppression by these cells of PLP reactive T cells.

In order to demonstrate that adoptively transferred Nogo-reactive T cells could cross into the CNS of animals with EAE, we immunized Thy1.1a SJL/J females with Nogo peptides or PLP139-151, collected draining lymph nodes 10 days later and restimulated whole lymphocytes in vitro with the immunizing antigen. We then intravenously administered 10 million Thy1.1a T cells into wild type (Thy1.2) SJL/J females that had been induced with EAE and were at peak of disease. Three days later we collected the CNS from these animals and looked at the presence of Thy1.1a cells in the CNS by immunohistochemistry. We could demonstrate the presence of adoptively transferred anti-PLP and anti-Nogo cells in several locations in the CNS of EAE animals, in the vasculature, peri-vascular infiltrates and in the parenchyma (FIG. 6B). From this we conclude that Nogo-reactive T cells are capable of migrating into the CNS of animals with active EAE, and that they might modulate disease locally, as opposed to the periphery.

Finally, we examined phenotype of anti-Nogo TCL by in vitro cytokine production essays. Briefly, anti-Nogop1-22 and anti-pNogo45-66 TCL were stimulated in vitro with their specific antigen in the presence of syngeneic irradiated antigen presenting cells. Supernatants were collected after 48 hours and cytokine production measured by ELISA. Results show that anti-pNogo spontaneously developed a Th2 phenotype, producing large amounts of IL4 and IL-10, whereas pNogo1-22 TCL show increased production of IFNγ (FIG. 6C).

Based on these results, adoptively transferred Nogo-reactive cells modulate ongoing EAE by migration into active demyelinating foci, where they encounter their specific antigen and differentiate into potentially beneficial phenotypes, which are capable of regulating the autoimmune response.

The above data show that the Nogo-66 sequence contains at least three antigenically important domains, capable of inducing a demyelinating autoimmune response in EAE susceptible mouse strains. These domains appear to be strain specific. SJL/J (H-2s) animals show a T cell reaction only to peptides Ng1-22 and Ng45-66, and C57BU6 (H-2b) animals to Ng1-22 and Ng23-44. We were able to demonstrate the existence of a T cell-response that is strong, specific and not cross-reactive with other known autoantigens, and of a B cell response that is also specific but exhibits marked epitope spreading to several other myelin antigens. Finally, we showed that T cells reactive to Nogo antigens are capable of ameliorating ongoing EAE induced with other antigens, presumably after migration to inflammatory sites and cross-regulation of other myelin reactive cells by adopting beneficial T helper 2 phenotypes.

In this sense, therefore, Nogo antigens appear to behave very similarly to other know myelin EAE antigens for these strains, such as PLP139-151 and MOG35-55, or the minor determinants MBP85-99, MOBP, OSP and CNPase. Unlike these antigens, however, apart from MAG and OMgp none of these other myelin proteins is known to play a role in axonal regrowth, and therefore the recognition of the possible contribution of Nogo-66 to CNS autoimmune demyelination is doubly important. First of all as an EAE antigen it might assume an important role regarding axonal pathology in this disease and in MS. Also, since modulating the immune response to Nogo-66 appears to be capable of ameliorating EAE, several antigen-specific therapeutic strategies might be devised to take advantage of this phenomenon to treat human autoimmune demyelinating diseases. Secondly, since immunization with Nogo peptides is capable of generating such a broad based B cell response to other myelin antigens, including MAG, vaccination with these antigens might have a useful role in improving axonal regeneration in CNS traumatic models, such as spinal cord injury. The phenomenon of epitope spreading of the B cell response after immunization with myelin antigens might mean in this context that even with single myelin antigen vaccination one could obtain a therapeutically important antibody response against several other potentially important neurite growth inhibitors, such as MAG.

Materials and Methods.

Mice. Female SJL/J and C57BU6 mice were obtained from Jackson laboratories (Maine) at 5 weeks of age. Mice were between 6 and 8 weeks of age when experiments were initiated. Nogo-A/B/C knockout mice were generated as described by Zheng et al (Zheng 2003). SJL/J Thy1.1a congenic mice were a kind gift from Harley Tse (Tse et al 1998).

Peptides. Nogo 1-22 (RIYKGVIQAIQKSDEGHPFRAY; SEQ ID NO:4), Nogo23-44 (LESEVAISEELVQKYSN-SALGH; SEQ ID NO:5), Nogo45-66 (VNSTIKELR-RLFLVDDLVDSLK; SEQ ID NO:2) PLP139-151; MBP85-99; and MOG35-55; peptides were synthesized by standard 9-fluorenylmethoxycarbonyl chemistry in our own facilities, HPLC purified and resuspended in PBS to 2mg/mi concentration.

Histology. Animals were killed by $CO_2$ overdose and perfused with 4% formalin, after which brain and spinal cord were dissected and stored. For standard histological techniques, samples were paraffin embedded before cutting and staining. Hematoxylin-eosin, Luxol fast blue and Bielschowsky stains were performed according to standard protocols. For Thy1.1a immunohistochemistry, CNS was snap-frozen in Tissue Tek (OCT) after partial immersion in liquid $N_2$. For staining, 8 μm criosections were stained with a biotinylated anti-Thy1.1a antibody conjugate (Pharmingen).

Immunization. For Nogo immunizations, SJL/J and C57BU6 female mice were injected subcutaneously with Nogo-peptide emulsions (concentrations ranging from 100 μg to 500 μg per injection) in CFA, consisting of IFA (Difco) and 1 mg/ml heat-inactivated *Mycobacterium tuberculosis* (strain H37RA; Difco laboratories, Detroit Mich.). Animals received two subcutaneous injections a week apart in different sites (flank and groin); at the time of the second immunization and 48 hours later, mice were injected intravenously with *Bordetella pertussis* toxin (List Laboratories) in PBS, 500 ng/animal; For Nogo-A/B/C knockouts, animals were immunized subcutaneously with 100 μg of MOG35-55 peptide emulsion in CFA and received two intravenous injections of 300 ng of *Bordetella pertussis* toxin, at the time of immunization and 48 hours later. Chronic EAE was induced in SJL/J mice by subcutaneous injection of 100 mg of PLP139-151 peptide emulsion in CFA. Animals were clinically scored daily according to the following scale: 0-normal; 1-tail paralysis; 2-hind limb paraparesis; 3-complete hind limb paralysis; 4-forelimb paresis or paralysis; 5-death.

Proliferation assays. Whole lymph node cells were cultured in 96-well microtiter plates at $0.5\times10^6$ cells/well. Culture medium consisted of RPMI 1640 supplemented with L-glutamine (2 mM), sodium pyruvate (1 mM), non-essential amino acids (0.1 mM), penicillin (100 U/ml), streptomycin (0.1 mg/ml), 2-ME ($5\times10^{-5}$ M) and 10% fetal bovine serum. Wells were pulsed with 1 μCi [$^3$H]TdR for the final 16 hours of culture, and incorporated radioactivity was measured using a betaplate scintillation counter.

REFERENCES

Fournier A E, GrandPre T. Strittmatter S M. Identification of a receptor mediating Nogo-66 inhibition of axonal regeneration. Nature 2001; 409: 341-346.

Chen M S, Huber A B, van der Haar M E, Frank M, Schnell L, Spillman A A, Christ F, Schwab M E. Nogo-A is a myelin-associated neurite outgrowth inhibitor and an antigen for monoclonal antibody IN-1. Nature 2000; 403: 434-439.

GrandPré T. Nakamura F, Vartanian T, Strittmatter S M. Identification of the Nogo inhibitor of axonal regeneration as a Reticulon protein. Nature 2000; 403: 439-444.

Brosamie C, Huber A B, Fiedler M, Skerra A, Schwab M E. Regeneration of lesioned corticospinal tract fibers in the adult rat induced by a recombinant, humanized IN-1 antibody fragment. J Neurosci 2000; 20(21): 8061-8068.

Brittis P A, Flanagan J G. Nogo domains and a Nogo receptor: implications for axon regeneration. Neuron, 2001 April; 30: 11-14.

Karim F, Volker D, Schwab M E. Improving axonal growth and functional recovery after experimental spinal cord injury by neutralizing myelin associated inhibitors. Brain Res Rev 2001; 36: 204-212.

Hauben E, Ibarra A, Mizrahi T, Barouch R, Agranov E, Schwartz M. Vaccination with a Nogo-A-derived peptide after incomplete spinal cord injury promotes recovery via a T-cell-mediated neuroprotective response: comparison with other myelin antigens. PNAS 2001 Dec. 18; 98(26): 15173-15178.

Merkler D, Metz G A S, Raineteau 0, Dietz V, Schwab M E, Fouad K. Locomotor recovery in spinal cord-injured rats treated with an antibody neutralizing the myelin-associated neurite growth inhibitor Nogo-A. J Neurosci 2001 May 15; 21(10): 3665-3673.

Huang D W, McKerracher L, Braun P E, David S. A therapeutic vaccine approach to stimulate axon regeneration in the adult mammalian spinal cord. Neuron 1999 November; 34: 639-647.

Zamvil S S, Steinman L. The T lymphocyte in experimental allergic encephalomyelitis. Annu Rev Immunol 1990; 8: 579-621.

Liu B P, Fournier A, GrandPre T, Strittmatter S M. Myelin-associated glycoprotein as a functional ligand for the Nogo-66 receptor. Science 2002 Aug. 16; 297: 1190-1193.

Morris-Downes M M, McCormack K, Baker D, Sivaprasad D, Natkuranajah J, Amor S. Encephalitogenic and immunogenic potential of myelin-associated glycoprotein (MAG), oligodendrocyte-specific glycoprotein (OSP) and 2',3'-cyclic nucleotide 3'-phosphodiesterase (CPNase) in ABH and SJL mice. J Neuroimmunol 2002; 122: 20-33.

Wang K C, Kim J A, Sivasankaran R, Segal R, He Z. P75 interacts with the Nogo receptor as a co-receptor for Nogo, MAG and OMgp. Nature 2002 Oct. 20

Fournier A E, Gould G C, Liu B P, Strittmatter S M. Truncated soluble Nogo receptor binds Nogo-66 and blocks inhibition of axon growth by myelin. J Neurosci 2002 Oct. 15; 22(20): 8876-8883.

Robinson W H, Steinman L, Utz P J. Protein and peptide array analysis of autoimmune disease. Biotechniques 2002 December; Suppl:66-9.

Robinson W H, DiGennaro C, Hueber W. Haab B B, Kamachi M, Dean E J, Fournel S, Fong D, Genovese M C, de Vegvar H E, Skriner K, Hirschberg D L, Morris R1, Muller S, Pruijn G J, van Venrooij W J, Smolen J S, Brown P O, Steinman L, Utz P J. Autoantigen microarrays for multiplex characterization of autoantibody responses. Nat Med 2002 March; 8(3): 295-301.

Steinman L. Multiple sclerosis: a two-stage disease. Nat Immunol 2001 September; 2(9): 762-4.

Steinman L. Assessment of animal models for MS and demyelinating disease in the design of rational therapy. Neuron 1999 November; 24(3): 511-4.

Ellezam B, Bertrand J, Dergham P, McKerracher L. Vaccination stimulates retinal ganglion cell regeneration in the adult optic nerve. Neurobiol Dis 2003 February; 12(1): 1-10.

Zheng B, Ho C, Li S, Keirstead H, Steward O, Tessier-Lavigne M. Lack of enhanced spinal regeneration in nogo-deficient mice. Neuron 2003 Apr. 24; 38(2): 213-24.

Domeniconi M, Cao Z, Spencer T, Sivasankaran R, Wang K, Nikulina E, Kimura N, Cai H, Deng K, Gao Y, He Z, Filbin M. Myelin-associated glycoprotein interacts with the Nogo66 receptor to inhibit neurite outgrowth. Neuron 2002 Jul. 18; 35(2):283-90.

Niederost B, Oertle T, Fritsche J, McKinney R A, Bandtlow C E. Nogo-A and myelin-associated glycoprotein mediate neurite growth inhibition by antagonistic regulation of RhoA and Rac1. J Neurosci 2002 Dec. 1; 22(23):10368-76.

Wang K C, Koprivica V, Kim J A, Sivasankaran R, Guo Y, Neve R L, He Z. Oligodendrocyte-myelin glycoprotein is a Nogo receptor ligand that inhibits neurite outgrowth. Nature 2002 Jun. 27; 417(6892):9414.

GrandPre T, Li S, Strittmatter S M. Nogo-66 receptor antagonist peptide promotes axonal regeneration. Nature 2002 May 30; 417(6888):547-51.

Steinman L, Martin R, Bernard C, Conlon P, Oksenberg J R. Multiple sclerosis: deeper understanding of its pathogenesis reveals new targets for therapy. Annu Rev Neurosci 2002; 25: 491-505.

Genain C P, Cannella B, Hauser S L, Raine C S. Identification of autoantibodies associated with myelin damage in multiple sclerosis. Nat Med 1999 February; 5(2):170-5.

Steinman L. Multiple Sclerosis: a coordinated immunological attack against myelin in the central nervous system. Cell 1996; 85: 299-302.

Trapp B D, Peterson J, Ransohoff R M, Rudick R, Mork S, Bo L. Axonal transection in the lesions of multiple sclerosis. N Engl J Med 1998 Jan. 29; 338(5):278-85.

Chang T T, Jabs C, Sobel R A, Kuchroo V K, Sharpe A H. Studies in B7-deficient mice reveal a critical role for B7 costimulation in both induction and effector phases of experimental autoimmune encephalomyelitis. J Exp Med 1999 Sep. 6; 190(5):733-40.

It is to be understood that this invention is not limited to the particular methodology, protocols, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a reagent" includes a plurality of such reagents and reference to "the reagent" includes reference to one or more reagents and equivalents thereof known to those skilled in the art, and so forth. All technical and scientific terms used herein have the same meaning as commonly understood to one of ordinary skill in the art to which this invention belongs unless clearly indicated otherwise.

All publications mentioned herein are incorporated herein by reference for the purpose of describing and disclosing, for example, the methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for.

Unless otherwise indicated, parts are parts by weight, molecular weight is average molecular weight, temperature is in degrees centigrade; and pressure is at or near atmospheric.

What is claimed is:

1. A pharmaceutical composition comprising a Nogo epitopic polypeptide or peptide consisting of the sequence SEQ ID NO:2 or SEQ ID NO:3.

* * * * *